United States Patent [19]

Grossman et al.

[11] Patent Number: 5,024,790
[45] Date of Patent: Jun. 18, 1991

[54] GLAZING DENTAL CONSTRUCTS

[75] Inventors: David G. Grossman, Corning; Michael A. Karnas, Big Flats, both of N.Y.; Ronald E. Johnson, Tioga, Pa.

[73] Assignee: Corning Incorporated, Corning, N.Y.

[21] Appl. No.: 550,288

[22] Filed: Jul. 9, 1990

[51] Int. Cl.$^5$ .............................................. A61C 13/09
[52] U.S. Cl. ........................................ 264/16; 264/20; 264/62; 264/510; 427/2
[58] Field of Search ...................... 264/16, 19, 20, 60, 264/62, 87, 131, 132, 553, 554, 571, 101, DIG. 50, DIG. 78, 510; 427/2, 193, 279, 376.2; 433/202.1, 203.1, 212.1

[56] References Cited

U.S. PATENT DOCUMENTS 3,769,055 10/1973 Blanco ................................ 427/147
4,481,227 11/1984 Tanaka ................................ 427/2

Primary Examiner—Jan H. Silbaugh
Assistant Examiner—Christopher A. Fiorilla
Attorney, Agent, or Firm—M. M. Peterson; C. S. Janes, Jr.

[57] ABSTRACT

A method of applying a surface glaze to a dental construct. The method includes associating glazing material with a carrier composed of a highly flexible and removable material, assembling the construct and carrier with the construct positioned within the carrier, forcing the carrier onto the construct by differential fluid pressure, removing the carrier, and maturing the glazing material to a glaze. The method finds particular application in applying coloration, either uniformly or in a pattern, to a dental construct.

25 Claims, 2 Drawing Sheets

GLAZING DENTAL CONSTRUCTS

RELATED APPLICATION

This application is related to patent application Ser. No. 07/550286, entitled GLAZING DENTAL CONSTRUCTS, filed of even date herewith in the names of D. G. Grossman and M. A. Karnas, and assigned to the same assignee as this application.

1. Field of the Invention

The field of the invention is dental restorations, more particularly, applying surface glazing to such articles.

2. Background

Preformed dental constructs may be produced in various forms, including crowns, veneers, inlays, onlays and false teeth. They may be constructed from a variety of materials, such as, ceramics, glass-ceramics, glass, porcelain, porcelain-fused-to metal (PFM), and organic materials.

Glass ceramics, found useful in producing dental constructs, are described, for example, in U.S. Pat. Nos. 3,732,087 (Grossman) and 4,431,420 (Adair). These patents disclose tetrasilicic fluormica glass-ceramics having properties particularly suited to producing such articles.

As described in the patents, a molten glass is cast in a mold by a process known as investment casting. The resulting glass construct is then thermally converted to a glass-ceramic. Normally, the construct is translucent and uncolored, but colorants may be included in the glass compositions, if desired.

Recently, a new system for the manufacture of crowns and other dental constructs has been proposed. This alternative to prior casting methods involves utilizing CAD/CAM techniques to provide computer-controlled milling of a solid block to a prescribed contour. Typical systems are described, for example, in European Patent Application 0/311/214/A1 (van der Zel) and U.S. Pat. No. 4,575,805 (Moermann et al.).

The present invention is particularly convenient to use with constructs prepared by this technique, but is not so limited. Rather, it is applicable to dental constructs by whatever manner produced and from whatever material employed.

While uncolored dental constructs are technically satisfactory, appearance frequently demands coloration for cosmetic effect. It is, of course, possible to include colorants in an original glass melt, as suggested in the Grossman and Adair patents. This provides a uniform coloration which may be acceptable for such purposes as small fillings or inlays.

For larger restorations, such as veneers, crowns and onlays, a more sophisticated system of coloration is desired. For example, color gradation from the neck of a crown to the incisal edge would be desirable. Also, special effects whereby the restoration would blend with the surrounding dentition could be very useful.

This desire for variable color effects has led to a search for a surface coloration technique. One such procedure is disclosed in U.S. Pat. No. 4,650,418 (Blair et al.). In this process, multiple layers of colored porcelain glazes are successively fired onto the outside surface of a restoration. In this way, distribution of color across the surface, as well as in depth, can be varied.

The process is effective, but requires a degree of artistic talent to arrange colors for a natural effect. Thus, a technician may use a brush to place or flow a wet porcelain glaze mixture where needed. It would, obviously, be desirable to provide a simpler procedure that requires less skill in application.

PURPOSES

A basic purpose is to provide an improved procedure for applying a surface glaze to a dental construct having a complex surface.

Another purpose is to provide a surface glazing procedure that is capable of producing special color effects.

A further purpose is to provide such a surface coloration procedure that involves a colorant application step that is predictable and reproducible.

A still further purpose is to provide such a surface coloration procedure that is readily adapted to automated processing.

Another purpose is to provide a preformed glazing device adapted to application of surface glazing to a dental construct.

Another purpose is to provide such a glazing device that may be adapted to produce special color effects.

SUMMARY OF THE INVENTION

In furtherance of these and other apparent purposes, our invention contemplates a method of glazing a dental construct having a complex surface which comprises associating glazing material with a carrier, the carrier being composed of a highly flexible and stretchable film or sheet of organic material, assembling the construct and carrier so that the construct is positioned adjacent to the carrier, subjecting the assembly to a differential pressure treatment to force the carrier into intimate contact with the construct surface, removing the organic carrier to leave the pattern of glazing material on the construct surface, and maturing the glazing material to a glaze on the construct surface.

The dental construct may be of any conventional material. Preferably, it is formed, either by investment casting or by milling, from a glass-ceramic, such as a tetrasilicic fluormica glass-ceramic.

The carrier may be formed from a thermoplastic elastomer (TPE) film. This film may have an elongation capability in the range of 100 to 1000% and a thickness of 0.5-2 mils. It should have a 100% secant modulus of less than 1000 psi. The inks applied to the carrier also must be stretchable.

The glazing material may be in the form of vitreous glaze particles if a clear glaze is desired. However, the main advantage of the invention is a means of coloration. In that embodiment, the glaze particles are admixed with one or more pigments, either uniformly dispersed, or arranged in a desired pattern. The glaze particles, with or without admixed pigments, may be either dispersed in the body of the carrier, or applied to the surface in the nature of a decal, that is, superjacent to a release layer on the carrier.

The differential pressure is preferably applied by creating a vacuum on the construct side of the carrier. In this embodiment, the construct may be placed upright on a vacuum plate, a central portion of the carrier is positioned above and in contact with, or in close proximity to, the construct, and a peripheral portion of the carrier is firmly clamped to form a vacuum seal. This peripheral clamped portion may, either prior to or subsequent to creating a vacuum around the construct, be lowered to near the same plane as the base of the construct. Optionally, additional pressure may be applied from an external source, such as through a pad or by positive air pressure, to the outside of the carrier.

PRIOR ART

Figure 1:
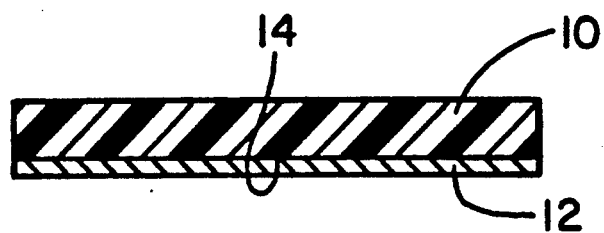
FIG. 1 is a view in cross-section of an organic carrier for use in practicing the invention.

In addition to the patents previously noted, the texts of which are incorporated herein by reference, the following United States Patents are cited of possible interest:

U.S. Pat. No. 2,391,106 (Saffir) discloses a method of forming an artificial tooth by forming a plastic resin sheath having the shape of a tooth, packing the sheath with a heat hardenable tooth material, and firing the assembly, to harden the tooth material and destroy the sheath. Here, the tooth is molded in the plastic sheath, rather than the sheath being molded on a preformed tooth.

U.S. Pat. No. 3,760,502 (Hirsch) discloses precolored, planar, veneer structures capable of being fastened to a crown for a tooth. Coacting fastening means are applied to the back of the veneer and to the front of the crown. There is no suggestion of conforming the veneer to the crown by differential pressure.

U.S. Pat. Nos. 3,986,261 (Faunce) and 4,226,593 (Cohen et al.) disclose directly applying a facing or veneer, which may be precolored, to a tooth. The tooth is etched, and a preformed, flexible veneer bonded to the etched surface of the tooth. There is no suggestion in these patents of applying differential pressure or of a surface coloring procedure.

U.S. Pat. No. 4,512,743 (Santucci et al.) discloses applying a pigmented, polymerizable composition to an etched tooth surface to form a veneer. Like Faunce and Cohen et al., this represents a form of directly applying a veneer to a tooth. It has no relation to forming of a dental construct as an independent body.

U.S. Pat. No. 4,822,279 (Greggs) discloses applying a custom-made porcelain veneer to a tooth. The veneer is stained and glazed by conventional techniques, thus providing no suggestion of the present procedure.

DESCRIPTION OF THE INVENTION

The present invention is a unique method of providing a glaze finish on a dental construct by applying glazing material over the surface of the construct and maturing the material. In one form, clear, or uncolored, vitreous glaze particles are applied, and the particles are fused into a glaze finish. In another form, one or more pigments are admixed in or with the glaze particles. This provides a glaze finish with any desired coloration pattern.

It is also possible, of course, to employ inks composed of curable organic materials which are sufficiently durable to function as the coloration after being cured by thermal means, or by radiation, such as visible light or ultra-violet light. This option is considered to be encompassed within the concept of glazing, and is particularly useful if the construct is also formed from an organic material.

The invention is described with respect to the use of vitreous glaze particles with pigment added, a particularly useful form in which the invention was developed. It will be understood that the same steps would be followed in producing a clear glaze, the single difference being omission of the pigment materials.

Dental shapes tend to have extremely irregular surfaces. Nevertheless, the present invention makes it possible to construct a highly flexible carrier that can be faithfully conformed to such a surface. This enables transfer of coloration to such an irregular surface. One convenient way of combining coloration materials with a carrier employs known decal constructions, such as described in U.S. Pat. No. 4,477,510. (Johnson et al.).

Highly flexible materials of construction for the carrier may be selected from the many high stretch plastics and thermoplastic elastomers (TPE) commercially available. These materials may be extruded, or may be blown, into satisfactory films to act as carriers for this application. Examples are linear low density polyethylene, polyethylene co-polymers such as EVA (ethylene vinyl acetate) and EEA (ethylene ethyl acrylate), as well as numerous thermoplastic elastomers (TPE). Satisfactory film materials for this application have elongations in the 100-1000% range, and are manufactured to within a thickness range of about 0.5-2 mils. For example, a TPU film (thermoplastic polyurethane) would be very satisfactory for this application in the thickness range of 1 mil.

The coloration inks, of course, would be printed onto the film, and release to the dental restoration surface would be effected by conventional means; i.e., silicone-release technology, or wax release upon application of heat. Another approach would be a water soluble stretch film, based on polyvinyl alcohol (PVA) or polyethylene oxide, which could be simply dissolved away after application. The inks would, of course, be water resistant in this case. It may also be possible to utilize a film with sufficiently clean burning characteristics to be simply removed by oxidation/degradation during the firing of the inks.

The inks for this application are envisioned as pigmented glass fluxes ground to a particle size range of 1-20 microns, and blended into an organic ink medium compatible with the film to be printed. The inks must either exhibit pressure-sensitivity (be sufficiently tacky to adhere simply through pressure) or must soften to become so upon the application of heat.

FIG. 1 is a view in cross-section of an organic film 10, in the nature of a decal, for use in carrying out the present invention. Film 10 has a pigmented layer 12 applied over its inner surface 14. This layer is composed of a mixture of a glaze and one or more pigments in particulate form. The glaze may be any conventional vitreous material adapted to being fired on the surface of a construct. It will be appreciated that, if a clear glaze is desired, the pigment will be omitted.

Pigmented layer 12 may be patterned in any desired manner. Thus, the amount of pigment, and hence the ultimate color intensity, may be graduated from the center of the film to its outer edge. Alternatively, where a mixed pigment is used, the mixture ratio may be varied.

A variety of other effects may also be achieved. Thus, intense underglaze stains may be placed in the grooves along the occlusal surface of a crown prior to application of film 10. Special effects, such as white check lines, or decalcification spots, may be placed on film 10 prior to application.

Figure 2:
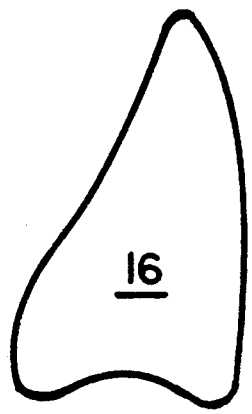
FIGS. 2 and 3 are, respectively, side and rear views of a dental construct for use in practicing the invention.
Figure 3:
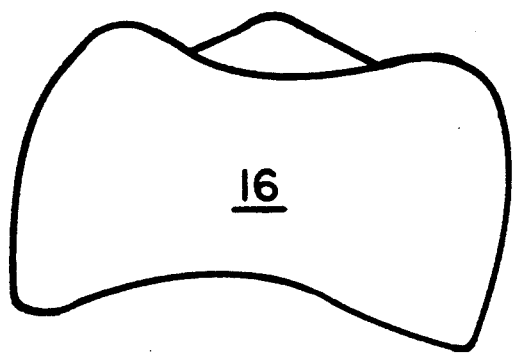

FIGS. 2 and 3 show a typical construct 16 preparatory to carrying out the coloration procedure. Construct 16 is shown as an unshaded crown adapted to placement on a patient's tooth. Crown 16 may be shaped in a conventional manner, or may be milled from a glass-ceramic or porcelain block by a CAD-CAM procedure such as referred to earlier.

FIG. 2 is an anterior view, and FIG. 3 a posterior view, of construct 16.

Figure 4:
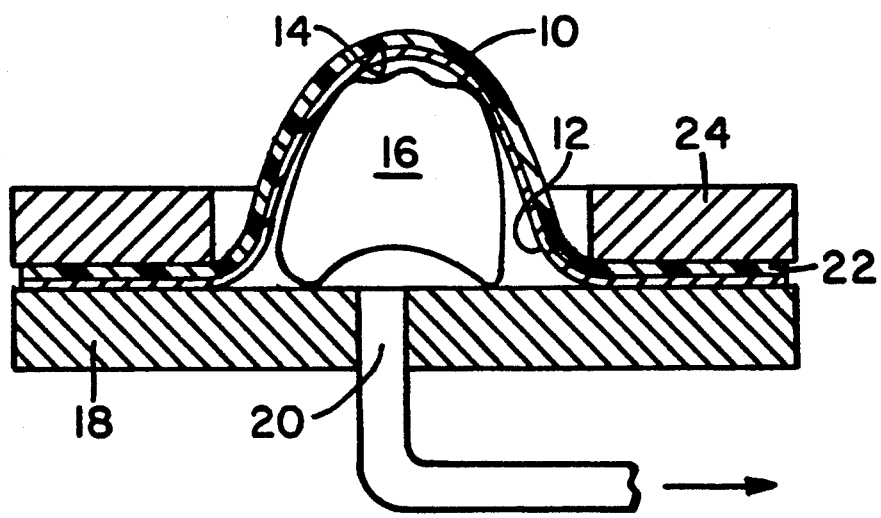
FIG. 4 is a view in cross-section of a vacuum apparatus assembled for practicing the invention.

FIG. 4 is a view in cross-section showing a typical vacuum system for applying a differential pressure in accordance with the invention. As here shown, construct 16 may be positioned on a plate 18 having an opening 20 to which vacuum connection may be made. Film 10 is then positioned over construct 16 with pigmented surface 14 facing construct 16. The central portion of film 10 rests on construct 16, while the periphery 22 is tightly secured between plate 18 and a circular ring clamp 24.

FIG. 4 shows the central portion of film 10 resting on construct 16. However, with an irregular surface, this could result in entrapment of air as the vacuum is applied. To avoid this, an alternative arrangement, as shown in FIGS. 5 and 6, may be employed.

Figure 5:
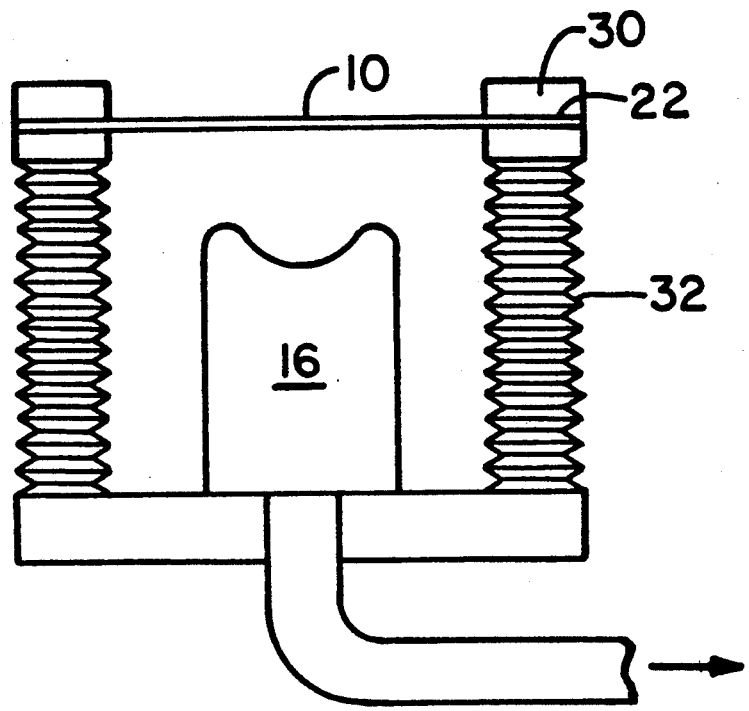
FIGS. 5 and 6 are schematic views of an alternative vacuum assembly for practicing the invention.

FIG. 5 shows film 10 with its periphery 22 securely held in a two-piece ring clamp 30. Ring clamp 30 is mounted on bellows 32, whereby film 10 is initially held above, although in rather close proximity to, construct 16.

Figure 6:
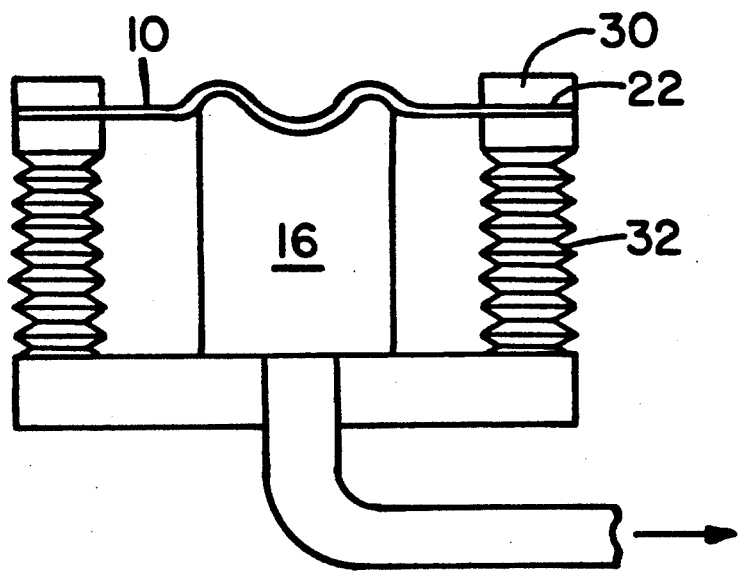

As a vacuum is drawn, the central portion of film 10 will be drawn against the upper surface of construct 16 as shown in FIG. 6. This avoids air entrapment. As further air is withdrawn, bellows 32 is collapsed, thus lowering the ring clamp 30, and thereby facilitating tight engagement between the film 10 and the side surface of construct 16.

In either arrangement, film 10 is drawn down against the surface of construct 16 as a vacuum is drawn. If necessary, further pressure may be applied through a pad in contact with the back surface of carrier 10 while it is in contact with the construct 16.

Once contact of film 10 with construct 16 surface is made, the use of a pad is simply a means to apply additional pressure to effect release. This may be particularly required in the case where release is effected by differences in surface energy between the article and film surface, as would be the case for conventional silicone release technology with pressure-sensitive adhesive inks. In the case of wax release, very little pressure is required and the pad would likely not be required, but rather in this case heat would be required to melt the wax release layer, as well as to soften the ink layer sufficiently to firmly adhere to the dental surface. It is also possible to use a water soluble film which can be dissolved away or a firable film (low residue) which can be fired (burned) away.

In the case where a pad is employed it is pressed against the back surface of the film in contact with the restoration in a rocking motion, multiple times over the various surfaces until full contact and adhesion is achieved. Although the use of a pad is preferred to insure adequate adhesion, it is not essential to this concept.

Where additional color is desired, or if special effects are desired, it is possible to apply additional layers by repeating the process. For example, a restoration may be deemed too light in color after one application. In that case, an additional layer may be applied by simply repeating the entire procedure. Alternatively, the second application may be another color, thus providing a blend.

We claim:

1. A method of glazing a dental construct having a complex surface which comprises associating glazing material with a carrier, the carrier being composed of a highly flexible and stretchable film or sheet of organic material, assembling the construct and carrier so that the construct is positioned adjacent the carrier, subjecting the assembly to a differential pressure treatment to force the carrier into intimate contact with the construct surface, removing the organic carrier to leave the glazing material on the construct surface, and maturing the glazing material to a glaze on the construct surface.

2. A method in accordance with claim 1 wherein the glazing material is in the form of vitreous glaze particles.

3. A method in accordance with claim 2 wherein the glaze particles are admixed with one or more pigments to form a coloration pattern.

4. A method in accordance with claim 1 wherein the glazing material is in the form of curable organic materials.

5. A method in accordance with claim 1 wherein the dental construct is formed from a glass-ceramic material.

6. A method in accordance with claim 5 wherein the glass-ceramic is a tetrasilicic fluormica.

7. A method is accordance with claim 1 wherein the dental construct is formed at least in part of a dental porcelain.

8. A method in accordance with claim 1 wherein the dental construct is formed from an organic material.

9. A method in accordance with claim 1 wherein the dental construct is formed from a ceramic material.

10. A method in accordance with claim 1 wherein the dental construct is formed from a blank by milling.

11. A method in accordance with claim 1 wherein the carrier is in the nature of a decal.

12. A method in accordance with claim 11 wherein the carrier decal is removed by a silicone release.

13. A method in accordance with claim 11 wherein the carrier decal is removed by wax release.

14. A method in accordance with claim 1 wherein the organic carrier is water soluble.

15. A method in accordance with claim 1 wherein the carrier is formed from a thermoplastic elastomer film.

16. A method in accordance with claim 1 wherein the carrier is formed from a film having an elongation capability in the range of 100 to 1000% and a thickness of 0.5 to 2 mils.

17. A method in accordance with claim 2 wherein the glaze particles, alone or mixed with pigment, are associated with the carrier by application to a surface of the carrier.

18. A method in accordance with claim 2 wherein the glaze particles, alone or mixed with pigment, are associated with the carrier by intermingling the particles with the body of the carrier.

19. A method in accordance with claim 3 wherein the coloration pattern is graduated across the carrier.

20. A method in accordance with claim 19 wherein the amount of pigment in the coloration pattern varies from the center of the carrier to the periphery.

21. A method in accordance with claim 1 wherein the differential pressure is applied by creating an enclosed space between the carrier and the construct and evacuating that space to draw the carrier into contact with the construct.

22. A method in accordance with claim 21 wherein the construct is placed upright on a vacuum plate, a central portion of the carrier is positioned above and in contact with, or in close proximity to, the construct, and a peripheral portion of the carrier is firmly held in place.

23. A method in accordance with claim 21 wherein additional force is applied by a source external to the carrier.

24. A method in accordance with claim 23 wherein the external source is a pad pressed against the carrier.

25. A method in accordance with claim 23 wherein the external source is positive air pressure applied against the reverse side of the carrier.

* * * * *